United States Patent
Kuroki et al.

(10) Patent No.: US 10,787,406 B2
(45) Date of Patent: Sep. 29, 2020

(54) COMPOSITION CONTAINING $C_8F_{17}BR$ AND METHOD FOR PRODUCING $C_8F_{17}BR$

(71) Applicant: DAIKIN INDUSTRIES, LTD., Osaka (JP)

(72) Inventors: Yoshichika Kuroki, Osaka (JP); Masahiro Higashi, Osaka (JP); Yoshihiro Yamamoto, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 16/626,642

(22) PCT Filed: Jul. 3, 2018

(86) PCT No.: PCT/JP2018/025177
§ 371 (c)(1),
(2) Date: Dec. 26, 2019

(87) PCT Pub. No.: WO2019/009278
PCT Pub. Date: Jan. 10, 2019

(65) Prior Publication Data
US 2020/0157028 A1    May 21, 2020

(30) Foreign Application Priority Data

Jul. 3, 2017 (JP) ................................ 2017-130363

(51) Int. Cl.
*C07C 19/14* (2006.01)
*C07C 17/20* (2006.01)
*C07C 17/395* (2006.01)

(52) U.S. Cl.
CPC ............ *C07C 19/14* (2013.01); *C07C 17/204* (2013.01); *C07C 17/395* (2013.01)

(58) Field of Classification Search
CPC ...... C07C 19/14; C07C 17/395; C07C 17/204
See application file for complete search history.

(56) References Cited

U.S. PATENT DOCUMENTS

| | | | |
|---|---|---|---|
| 5,072,062 A | 12/1991 | Kumai et al. | |
| 5,073,651 A | 12/1991 | Raab | |
| 5,688,379 A | 11/1997 | Furutaka et al. | |
| 2006/0100464 A1* | 5/2006 | Shtarov | C07C 29/86 568/914 |
| 2009/0197201 A1 | 8/2009 | Hierse et al. | |
| 2010/0292393 A1* | 11/2010 | Murata | C07C 67/08 524/544 |

FOREIGN PATENT DOCUMENTS

| | | |
|---|---|---|
| JP | 60-184033 | 9/1985 |
| JP | 3-287551 | 12/1991 |
| JP | 6-234671 | 8/1994 |
| JP | 2008-519079 | 6/2008 |
| JP | 2009-541399 | 11/2009 |
| WO | 2006/052567 | 5/2006 |

OTHER PUBLICATIONS

International Search Report dated Aug. 21, 2018 in International (PCT) Application No. PCT/JP2018/025177.
Prevedouros et al., "Sources, Fate and Transport of Perfluorocarboxylates", Environmental Science & Technology, 2006, vol. 40, No. 1, pp. 32-44.
Office Action dated Jun. 1, 2020 in corresponding Indian Patent Application No. 202047002585, with English Translation.

* cited by examiner

*Primary Examiner* — Jafar F Parsa
(74) *Attorney, Agent, or Firm* — Wenderoth, Lind & Ponack, L.L.P.

(57) ABSTRACT

This invention provides a composition that contains PFOB with a PFOA content lower than that of known PFOB, and that is less likely to have an adverse effect on the environment; and provides a method for producing PFOB. The composition contains $C_8F_{17}Br$ and further contains $C_7F_{15}COOH$, wherein $C_7F_{15}COOH$ is present in a concentration of 25 ppb or less based on the total weight of $C_8F_{17}Br$. The method for producing $C_8F_{17}Br$ comprises reacting $C_8F_{17}I$ and a brominating agent to obtain $C_8F_{17}Br$, and alkali-washing the obtained $C_8F_{17}Br$ to reduce the $C_7F_{15}COOH$ content to 25 ppb or less based on the total weight of $C_8F_{17}Br$.

6 Claims, No Drawings

COMPOSITION CONTAINING $C_8F_{17}BR$ AND METHOD FOR PRODUCING $C_8F_{17}BR$

TECHNICAL FIELD

The present invention relates to a composition containing $C_8F_{17}Br$, and a method for producing $C_8F_{17}Br$.

BACKGROUND ART

Perfluorooctyl bromide (abbreviated as "PFOB"), represented by the formula: $C_8F_{17}Br$, is known as a compound having X-ray contrast ability and MR contrast ability. It is also known that PFOB can be used as an active pharmaceutical ingredient of a diagnostic drug, a medicinal intermediate, and the like.

It is known that PFOB can be produced by various methods. Examples of known methods of obtaining PFOB include a method of reacting a compound represented by the formula: $C_8F_{17}I$ (n-perfluorooctyl iodide, abbreviated as "PFOI") with a brominating agent, such as bromine, in a gas phase (e.g., Patent Literature (PTL) 1); and a method of obtaining PFOB by performing photochemical bromination of PFOI (e.g., PTL 2).

CITATION LIST

Patent Literature

PTL 1: JPH03-287551A
PTL 2: JPH06-234671

SUMMARY OF INVENTION

Technical Problem

However, as a result of a detailed analysis of the production of PFOB using PFOI as a starting material, the present inventors found that under conditions in which at least water and/or oxygen are present, PFOI used as a starting material undergoes decomposition due to the action of light or heat, and undesirably forms perfluoro-octanoic acid (PFOA; $C_7F_{15}COOH$). When PFOB is produced using such a starting material containing PFOA, PFOA is easily incorporated in the reaction product, and the purity of PFOB is easily reduced. To minimize the amount of PFOA in PFOB, for example, an additional step is required for separately purifying PFOI; or strict control is required for the storage method or storage time for PFOI used as a starting material. Furthermore, since PFOA is known as a compound that is likely to have an adverse effect on the environment, it is considered significantly important to provide PFOB containing a smaller amount of PFOA.

The present invention has been accomplished in view of the above. An object of the present invention is to provide a composition containing PFOB with a small amount of PFOA as an impurity, and a method for producing the PFOB.

Solution to Problem

In order to achieve the above object, the present inventors conducted extensive research, and consequently found that the above object can be achieved by a washing process by which PFOA is efficiently removed from PFOB. The present invention has been accomplished based on this finding.

More specifically, the present invention encompasses the inventions according to the following items.

Item 1. A composition containing $C_8F_{17}Br$, and further containing $C_7F_{15}COOH$, wherein $C_7F_{15}COOH$ is present in a concentration of 25 ppb or less based on the total weight of $C_8F_{17}Br$.

Item 2. A method for producing $C_8F_{17}Br$, comprising:
reacting $C_8F_{17}I$ and a brominating agent to obtain $C_8F_{17}Br$; and
alkali-washing the obtained $C_8F_{17}Br$ to reduce the $C_7F_{15}COOH$ content to 25 ppb or less based on the total weight of $C_8F_{17}Br$.

Item 3. The production method according to Item 2, wherein the alkali-washing is performed using an alkali solution having a concentration of 0.01 to 98 wt %.

Advantageous Effects of Invention

The composition containing $C_8F_{17}Br$ (PFOB) of the present invention contains a small amount of $C_7F_{15}COOH$ (PFOA), and the purity of PFOB is high; therefore, the composition of the present invention is less likely to have an adverse effect on the environment.

According to the method for producing PFOB of the present invention, the PFOA content is easily reduced to 25 ppb or less based on the total weight of PFOB, and high-purity PFOB is produced with a simple process.

DESCRIPTION OF EMBODIMENTS

Specific embodiments of the present invention are described in detail below. In this specification, the expressions "comprise" and "contain" encompass the concepts of "comprise," "contain," "consist essentially of," and "consist of."

1. Composition Containing $C_8F_{17}Br$

The composition containing $C_8F_{17}Br$ of the present invention further contains $C_7F_{15}COOH$, and the $C_7F_{15}COOH$ content is 25 ppb or less based on the total weight of $C_8F_{17}Br$. As stated later, $C_7F_{15}COOH$ can serve as an impurity component in the composition. Otherwise, $C_7F_{15}COOH$ may be, for example, a by-product during the production of $C_8F_{17}Br$. Alternatively, $C_7F_{15}COOH$ may be, for example, a component intentionally added to the composition.

In this specification, $C_8F_{17}Br$ (perfluorooctyl bromide) is abbreviated as "PFOB," and $C_7F_{15}COOH$ (perfluoro-octanoic acid) is abbreviated as "PFOA." Further, a compound represented by the formula: $C_8F_{17}I$ (n-perfluorooctyl iodide) mentioned later is abbreviated as "PFOI."

In the composition of the present invention, there is no limitation on the method of adjusting the PFOA content to be 25 ppb or less based on the total weight of PFOB, and various methods can be widely used. In particular, the purification step mentioned below in section "2. Method for Producing $C_8F_{17}Br$" is suitably used. In this case, although PFOI containing PFOA is used as a starting material, high-purity PFOB with a low PFOA content can be obtained, and the PFOA content can be easily adjusted to 25 ppb or less based on the total weight of PFOB.

In the composition of the present invention, the upper limit of the PFOA content based on the total weight of PFOB is preferably 20 ppb, 15 ppb, 10 ppb, 5 ppb, 3 ppb, 2 ppb, 1 ppb, 0.5 ppb, 0.2 ppb, 0.1 ppb, 0.05 ppb, and 0.01 ppb, in descending order of preference. Furthermore, in the composition of the present invention, the upper limit of the PFOA content based on the total weight of PFOB can be 0.001 ppb.

In the composition of the present invention, if the PFOA content exceeds 25 ppb based on the total weight of PFOB, PFOA may possibly have an adverse effect on the environment, and the usage etc. of PFOB is restricted; therefore, a PFOA content exceeding 25 ppb is not preferable.

There are believed to be various reasons why PFOA can be present as an impurity in PFOB. In particular, when PFOI is used as a starting material to produce PFOB, the produced PFOB is likely to contain a large amount of PFOA. This is because PFOI is a compound unstable to light and heat; and, due to the action of either light or heat, or both light and heat, PFOI undergoes a reaction with oxygen or oxygen present in the air and/or water, and easily decomposes into PFOA. In the presence of oxygen and/or water, in particular, PFOI is liable to decompose into PFOA.

As long as the effects of the present invention are not impaired, the composition of the present invention may contain a compound other than PFOB, such as known additives etc. When the composition of the present invention contains a compound etc. other than PFOB, the composition of the present invention can contain PFOB in an amount of 50 wt % or more, preferably 80 wt % or more, more preferably 90 wt % or more, and particularly preferably 99 wt % or more, based on the total weight of the composition. The composition of the present invention may consist only of PFOB containing 25 ppb or less of PFOA.

The method for preparing the composition of the present invention is not limited. For example, the composition of the present invention can be prepared by the method for producing $C_8F_{17}Br$ described below.

2. Method for Producing $C_8F_{17}Br$

The method for producing $C_8F_{17}Br$ (PFOB) of the present invention is not limited.

For example, the method for producing PFOB of the present invention may comprise
reacting $C_8F_{17}I$ and a brominating agent to obtain $C_8F_{17}Br$; and alkali-washing the obtained $C_8F_{17}Br$ to reduce the $C_7F_{15}COOH$ content to 25 ppb or less based on the total weight of $C_8F_{17}Br$. The reaction product obtained through this production method is PFOB ($C_8F_{17}Br$) containing PFOA ($C_7F_{15}COOH$) as an impurity, and the PFOA content, in particular, is 25 ppb or less based on the total weight of PFOB.

Hereinafter, the step of reacting $C_8F_{17}I$ (PFOI) and a brominating agent to obtain $C_8F_{17}Br$ is referred to as "the reaction step," and the step of alkali-washing the obtained $C_8F_{17}Br$ to reduce the $C_7F_{15}COOH$ content to 25 ppb or less based on the total weight of $C_8F_{17}Br$ is referred to as "the purification step."

In the reaction step, PFOI is reacted with a brominating agent to produce PFOB.

The brominating agent is not limited, and bromine, for example, can be used. Additionally, a compound that releases bromine can also be used. Examples of the compound that releases bromine include IBr and $IBr_3$, N-bromosuccinimide, N-bromophthalimide, dibromoisocyanuric acid, 1,3-dibromo-5,5-dimethylhydantoin, N-bromoacetamide, N-bromosaccharin, and the like. The brominating agent is preferably bromine.

The PFOI used in the reaction step may be produced, for example, by using known methods; or may be commercially available PFOI. As described above, PFOI contains PFOA as an impurity. Thus, for example, PFOI can be purified in advance before use. In the production method of the present invention, however, PFOA as an impurity is easily removable in the purification step after the reaction step. Therefore, PFOI can be subjected to the reaction step without purifying the PFOI in advance. This can make the entire production process simpler.

PFOI as a starting material forms PFOA due to the action of light and/or heat during storage; thus, it is important to strictly control the storage conditions for PFOI. However, according to the purification step of the production method of the present invention, the PFOA content can be easily reduced, and thus the storage conditions for PFOI are not necessarily strictly controlled.

The ratio of PFOI to a brominating agent is not limited. For example, a brominating agent can be used in an amount of 1 to 10 mol, and preferably 1 to 5 mol, per mol of PFOI.

The reaction of PFOI and a brominating agent can be carried out, for example, in the presence of an inert gas, such as nitrogen.

The reaction of PFOI and a brominating agent can be carried out, for example, by a method of heating an optically transparent reactor containing PFOI, and adding a brominating agent thereto dropwise while being exposed to light. However, the method is not limited thereto; for example, it is also possible to use a method of heating without exposure to light. When heating is performed without exposure to light, the reaction proceeds even at a heating temperature of, for example, about 140° C. The brominating agent can be supplied in divided portions such that a portion of brominating agent is supplied to a reactor in advance, followed by a further addition of an additional amount. The reaction of PFOI and a brominating agent can also be carried out continuously. Examples of the optically transparent reactor include various glass reactors, such as a glass flask and a glass tube. The reaction of PFOI and a brominating agent can be carried out in a gas phase.

The temperature for heating the reactor, i.e., the reaction temperature, is not limited. The temperature is preferably a temperature at which PFOI is allowed to reflux, i.e., 80 to 180° C., and particularly preferably 130 to 160° C. The time for reacting PFOI and a brominating agent is not limited.

For exposure to light in the reaction of PFOI and a brominating agent, it is possible to use light with a wavelength of 1 µm or less (preferably 0.2 to 0.7 µm), such as visible light and ultraviolet light.

The reaction product obtained from the reaction of PFOI and a brominating agent contains PFOB, which is a target product. In the reaction product, IBr etc. are also generated as by-products. Further, since PFOI contains PFOA as an impurity, as stated above, the reaction product obtained after the reaction can also contain PFOA. The reaction product obtained in the reaction step is subjected to the purification step.

In the purification step, PFOB obtained in the reaction step is alkali-washed. In this purification step, the PFOA content in the reaction product can be reduced to 25 ppb or less based on the total weight of PFOB.

The method for alkali-washing is not limited. Examples include a method in which an alkali solution is added to the reaction product, the resulting mixture is stirred and then allowed to stand to separate it into two layers, i.e., a layer containing the reaction product, and a layer of the alkali solution (sometimes referred to as "the alkali layer"); and the layer containing the reaction product is collected by separation. In this manner, PFOB as a reaction product can be obtained. Alternatively, the layer containing PFOB, i.e., a reaction product, can also be obtained by adding an alkali solution to the reaction product, followed by distillation.

The series of operations from the operation of adding an alkali solution to the operation of collecting the layer containing the reaction product by separation is referred to as "alkali-washing."

The alkali-washing is preferably performed several times. In this case, a reaction product of higher purity is obtained; in particular, the amount of PFOI is more easily reduced to a desired amount. More specifically, alkali-washing is preferably repeated so that the alkali layer after alkali-washing has a pH of 7 or more, preferably 8 or more, and particularly preferably 10 or more.

The type of alkali used for alkali-washing is not limited, and known bases can be widely used. Examples include sodium hydroxide, potassium hydroxide, calcium hydroxide, sodium carbonate, potassium carbonate, calcium carbonate, ammonia, ammonium carbonate, sodium hydrogen carbonate, potassium hydrogen carbonate, ammonium bicarbonate, and other inorganic bases. Additionally, for alkali, it is also possible to use organic bases, such as organic amines, basic amino acids, and metal alkoxides.

When an alkali solution is used for alkali-washing, the solvent of the alkali solution may be water, an alcohol, or a mixed solvent thereof. Examples of alcohol include lower alcohols, such as methanol, ethanol, and isopropanol.

The concentration of the alkali solution used for alkali-washing is not limited. To more easily reduce the PFOA content in the reaction product, alkali-washing is performed using an alkali solution having a concentration of 0.01 to 98 wt %, and more preferably 0.01 to 48 wt %. The concentration of alkali solution is more preferably 25 wt % or less, still more preferably 10 wt % or less, particularly preferably 5 wt % or less, and most preferably 4.5 wt % or less. The concentration of alkali solution is more preferably 1 wt % or more, and particularly preferably 2 wt % or more.

During alkali-washing in the purification step, PFOA contained in the reaction product is removed; additionally, IBr as a by-product can also be removed.

After alkali-washing, the reaction product is optionally washed with a solution containing an inorganic salt. Examples of inorganic salts include sodium chloride, potassium chloride, and the like. By washing with a solution containing an inorganic salt, the pH of the reaction product after alkali-washing can be adjusted, and water can also be removed.

In the purification step, after the alkaline treatment, the reaction product may be further subjected to drying treatment and distillation treatment. The drying treatment can be performed by, for example, a method of adding a drying agent to the reaction product. The type of drying agent is not limited. Examples include anhydrous magnesium sulfate. The distillation treatment can be performed, for example, after the drying treatment. The method of distillation treatment is not limited, and known distillation methods can be widely used.

By performing the purification step, PFOB is purified, and high-purity PFOB containing 25 ppb or less of PFOA as an impurity can be produced.

In particular, according to the production method of the present invention, although PFOI containing PFOA is used as a starting material to produce PFOB, the resulting PFOB contains a small amount of PFOA, and high-purity PFOB can be obtained. Further, according to the production method of the present invention, the amount of PFOA can be easily reduced by purification; thus, PFOI whose storage conditions are not strictly controlled can be used as a starting material.

The PFOB obtained by using the production method of the present invention is suitably used, for example, as a starting material for preparing the composition containing PFOB of the present invention. In particular, the PFOA content in the PFOB is less than that of known PFOB, and the PFOB of the present invention is less likely to have an adverse effect on the environment. Accordingly, the PFOB is less likely to be affected by environmental regulations etc.

The composition containing PFOB of the present invention and the PFOB obtained by the production method of the present invention are suitably used for various applications, such as an active pharmaceutical ingredient of a diagnostic drug, a medicinal intermediate, etc., using the characteristics of PFOB, such as X-ray contrast ability and MR contrast ability.

EXAMPLES

The present invention is described in more detail below with reference to Examples. However, the present invention is not limited to the embodiments in the Examples.

Example 1

PFOI (1760 g) was supplied to a reaction vessel, the reaction vessel was heated to 140 to 142° C., and the PFOI in the reaction vessel was stirred. Subsequently, 1000 to 1600 g of bromine was supplied to this reaction vessel in several divided portions; and the mixture was heated to reflux, so that the PFOI was brominated.

After the completion of bromination, the reaction solution was cooled, and alkali-washed. In this alkali-washing, first, about 0.5 L of a 2 to 3 wt % sodium hydroxide aqueous solution was added to the obtained reaction solution, followed by stirring. Thereafter, stirring was stopped, and the reaction vessel was allowed to stand to separate the mixture into a layer containing the reaction product and a layer of the sodium hydroxide aqueous solution. Then, the layer containing the reaction product was extracted by separation. This alkali-washing was repeated until the pH of the layer of the sodium hydroxide aqueous solution exceeded 8.

Thereafter, the reaction product was washed by adding about 0.3 L of brine whose concentration was adjusted to 7 to 10%. Subsequently, the layer containing the reaction product was collected. About 20 g of anhydrous magnesium sulfate was added to the collected layer containing the reaction product, and the mixture was stirred. Thereafter, the layer containing the reaction product was collected through filtration, followed by distillation to obtain 1500 g of PFOB.

The concentration of PFOA in the obtained PFOB was analyzed by LC-MS/MS. The concentration of PFOA was 5 ppb or less based on the total weight of PFOB.

Example 2

PFOB (1500 g) was obtained as in Example 1, except that PFOI was changed to PFOI containing 350 ppm by weight of PFOA.

The concentration of PFOA in the obtained PFOB was analyzed by LC-MS/MS. The concentration of PFOA was 5 ppb or less based on the total weight of PFOB.

The invention claimed is:
1. A composition containing $C_8F_{17}Br$, and further containing $C_7F_{15}COOH$, wherein $C_7F_{15}COOH$ is present in a concentration of 25 ppb or less based on the total weight of $C_8F_{17}Br$.

2. A method for producing $C_8F_{17}Br$, comprising:

reacting $C_8F_{17}I$ and a brominating agent to obtain $C_8F_{17}Br$; and alkali-washing the obtained $C_8F_{17}Br$ to reduce the $C_7F_{15}COOH$ content to 25 ppb or less based on the total weight of $C_8F_{17}Br$.

3. The production method according to claim 2, wherein the alkali-washing is performed using an alkali solution having a concentration of 0.01 to 98 wt %.

4. The production method according to claim 2, wherein the alkali-washing is performed using an alkali solution having a concentration of 0.01 to 48 wt %.

5. The production method according to claim 2, wherein the alkali-washing is performed using an alkali solution having a concentration of 0.01 to 25 wt %.

6. The production method according to claim 2, wherein the alkali-washing is performed using an alkali solution having a concentration of 0.01 to 10 wt %.

* * * * *